United States Patent [19]

Carabelli et al.

[11] Patent Number: 4,627,109

[45] Date of Patent: Dec. 9, 1986

[54] LUMBOSACRAL SUPPORT

[75] Inventors: Robert A. Carabelli, Cherry Hill Medical Arts Bldg., 7740 Maple Ave., Pennsauken, N.J. 08109; Allan G. Edmund, Ocean City, N.J.

[73] Assignee: Robert A. Carabelli, Philadelphia, Pa.

[21] Appl. No.: 784,337

[22] Filed: Oct. 4, 1985

[51] Int. Cl.⁴ .............................................. A61F 5/02
[52] U.S. Cl. ............................................ 2/44; 2/300; 128/78
[58] Field of Search ....................... 2/44, 300; 128/78

[56] References Cited

U.S. PATENT DOCUMENTS

| 2,056,767 | 10/1936 | Blath | 2/44 X |
| 2,250,267 | 7/1941 | Lins | 2/44 X |
| 3,554,190 | 1/1971 | Kaplan | 2/44 X |
| 4,080,962 | 3/1978 | Berkeley | 2/44 X |
| 4,175,553 | 11/1979 | Rosenberg | 2/44 X |
| 4,384,372 | 5/1983 | Rector | 2/300 |

FOREIGN PATENT DOCUMENTS

| 0251685 | 9/1962 | Australia | 2/44 |
| 0850541 | 12/1939 | France | 2/44 |

*Primary Examiner*—Louis K. Rimrodt
*Attorney, Agent, or Firm*—Norman E. Lehrer

[57] ABSTRACT

A lumbosacral support includes an elastic belt adapted to be worn around a person's waist and includes Velcro fasteners at its ends. The belt carries a double layer foam pad adjacent the middle thereof which is adapted to lie against the wearer's lower back. A vertically extending trough-like groove is cut away from the central portion of the pad. The pad directly overlies the wearer's spine whereby when the wearer presses against a seat back, the pad puts pressure on the supporting lumbosacral musculature on either side of the spine but does not put pressure directly on the spinal column.

9 Claims, 8 Drawing Figures

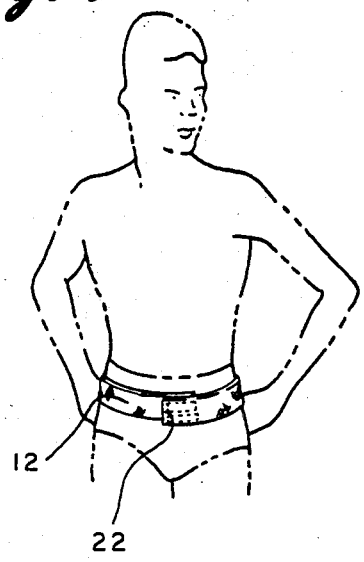
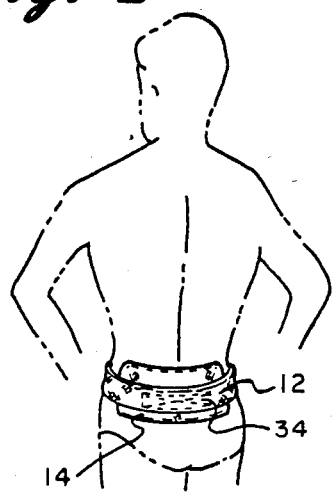
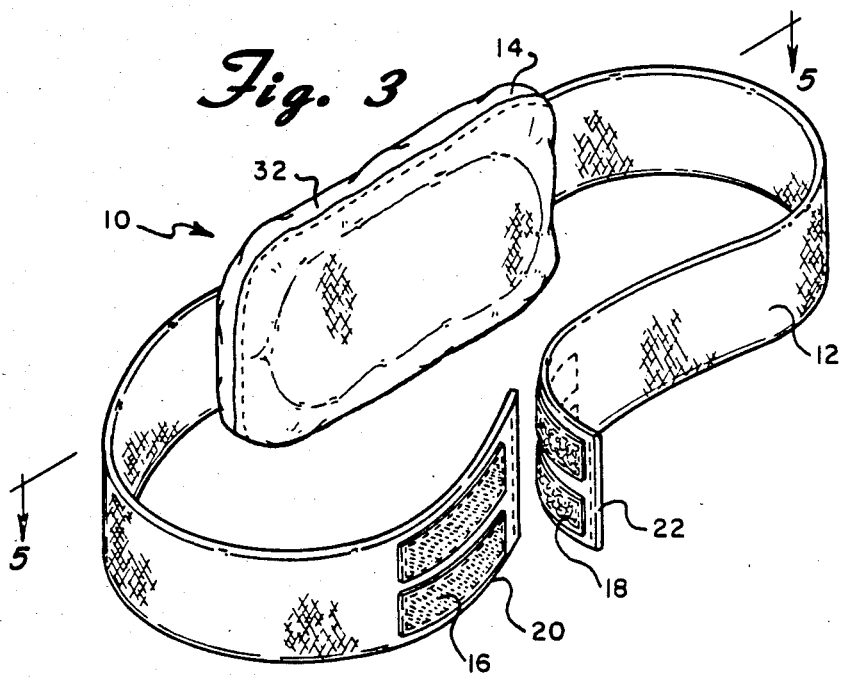

LUMBOSACRAL SUPPORT

BACKGROUND OF THE INVENTION

The present invention is directed toward a lumbosacral support and more particularly toward a lumbosacral support in the form of a belt which is intended to be worn by a person suffering from lower back pain or to prevent lower back pain.

Lumbosacral support belts have been known and used for many years. Such devices are shown, for example, in U.S. Pat. Nos. 1,924,640; 3,096,760; 3,154,072 and 4,384,372.

Substantially all known devices of this type are comprised of a belt which carries a foam or similar pad adjacent the midportion thereof. When the belt is worn around a person's waist, the pad overlies the spine in the lower portion of the person's back. As a result, these devices put pressure directly on the spine creating stress on the spinal column and nerves.

Other devices have been proposed which allow pressure to be placed only on selected areas of the back. One such device is shown, for example, in U.S. Pat. No. 4,178,923. However, the construction of this device is relatively complex thereby making it relatively difficult and expensive to manufacture.

SUMMARY OF THE INVENTION

The present invention is directed toward a lumbosacral support for maintaining the lordotic curve to reduce back fatigue and which overcomes the deficiencies of the prior art described above. The inventive support includes an elastic belt adapted to be worn around a person's waist and includes Velcro fasteners at its ends. The belt carries a double layer foam pad adjacent the middle thereof which is adapted to lie against the wearer's lower back. A vertically extending trough-like groove is cut away from the central portion of the pad. The pad directly overlies the wearer's spine whereby when the wearer presses against a seat back, the pad puts pressure on the supporting lumbosacral musculature on either side of the spine but does not put pressure directly on the spinal column.

BRIEF DESCRIPTION OF THE DRAWINGS

For the purpose of illustrating the invention, there are shown in the accompanying drawings two forms which are presently preferred; it being understood that the invention is not intended to be limited to the precise arrangements and instrumentalities shown.

FIG. 1 is a front perspective view of a person wearing the lumbosacral support of the present invention;

FIG. 2 is a rear perspective view thereof;

FIG. 3 is a perspective view of the support not being worn but arranged in a position similar to that in which it is worn;

DETAILED DESCRIPTION OF THE PREFERRED EMBODIMENTS

Figure 4:
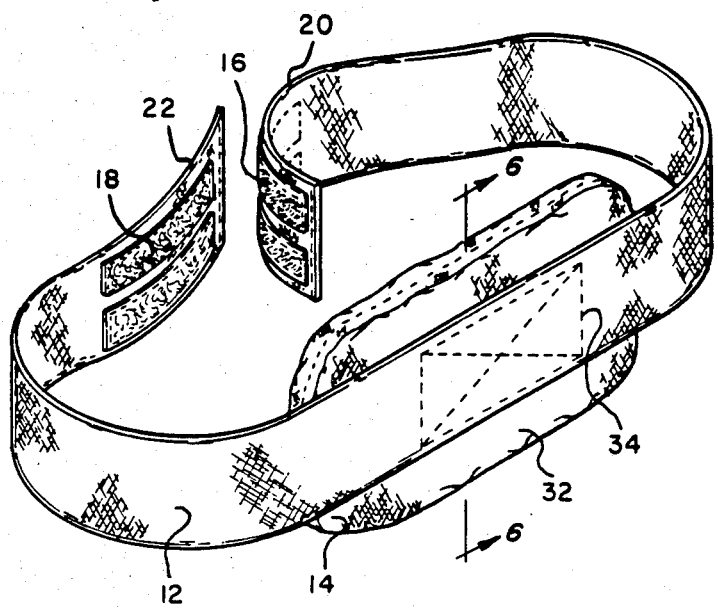
FIG. 4 is a rear perspective view of the device as shown in FIG. 3.

Referring now to the drawings in detail wherein like reference numerals have been used throughout the various figures to designate like elements, there is shown in FIGS. 1–4 a first embodiment of a lumbosacral support constructed in accordance with the principles of the present invention and designated generally as 10. The lumbosacral support 10 is comprised essentially of two parts: a belt 12 and a support pad 14 which is carried by the belt 12 adjacent its midportion.

As shown most clearly in FIGS. 1 and 2, the belt 12 has a length which is sufficient to allow the same to wrap around the abdomen or waist of the person wearing the device. It is preferably comprised of a lightweight flexible elastic material to enable the same to conform to various sizes. The belt 12 may be between one and six inches in height but is preferably about three inches.

Velcro fasteners 16 and 18 are sewn onto the ends 20 and 22 of the belt 12. The fasteners 16 and 18 are preferably in the form of elongated strips as shown most clearly in FIGS. 3 and 4. This also adds to the adjustability of the belt 12.

The support pad 14 is comprised of a pair of foam pad layers 24 and 26 which are preferably bonded or cemented together. The foam pad layer 24 which is closer to the belt 12 is comprised of a relatively rigid urethane-type foam such as a material sold under the trademark Plastazote. The foam layer 26 which is adapted to be closer to the person's back when the belt is worn is also preferably comprised of urethane foam or similar material. However, foam layer 26 is substantially softer and more pliable and compressible than the layer 24.

Figure 6:
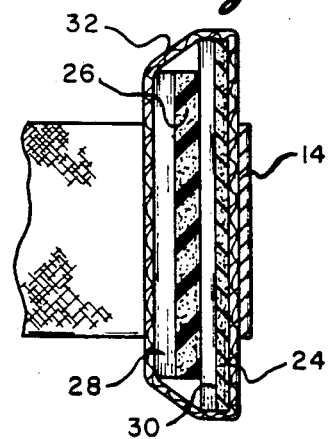
FIG. 6 is a cross-sectional view taken through the line 6—6 of FIG. 4.
Figure 5:
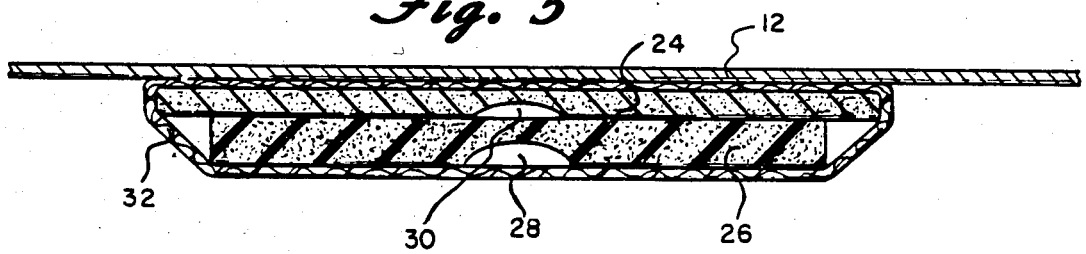
FIG. 5 is a cross-sectional view taken through the line 5—5 of FIG. 3.

As shown most clearly in FIGS. 5 and 6, a trough-like groove 28 is cut away from the central portion of the foam layer 26. The groove 28 extends substantially vertically throughout the entire height of the pad 26. A similar vertically extending groove 30 is formed in the front surface of the foam layer 24. As will be explained more fully hereinafter, the trough-like grooves 28 and 30 allow the device to bend slightly to the contour of the person's back. In addition, they are intended to directly overlie the spine and prevent pressure from being applied directly to the spinal column.

The foam pad layers 24 and 26 are substantially rectangular or oval shaped as shown. They may have a length of approximately between six and twelve inches and a height of between four and eight inches. The depth or thickness of the combined layers is approximately two inches. Preferably, the outer less dense layer 26 is substantially thicker than the inner denser layer 24; the layer 24 functioning primarily as a substrate to support the layer 26.

Both foam layer pads 24 and 26 are covered with a flexible fabric material 32. This fabric material 32 is, in turn, sewn or otherwise secured to the midportion of the belt 12 such as shown by the stitching 34 (FIGS. 2 and 4).

The lumbosacral support 10 of the present invention is used in the following manner. As shown in FIGS. 1 and 2, the belt 12 wraps around the person's waist or abdomen and the ends 20 and 22 thereof are fastened together at the front. The support pad 14 is positioned at the lower back in the lumbosacral area which is immediately below the thoracic region and immediately above the buttock region. The pad 14 is arranged so that the grooves 28 and 30 directly overlie and are in substantial alignment with the person's spine. When the person wearing the device presses against a seat back or lies down on his back, the pad 14 puts pressure on the supporting lumbosacral musculature on either side of the spine but, as a result of the grooves 28 and 30 does not put pressure directly on the spinal column.

Figure 7:
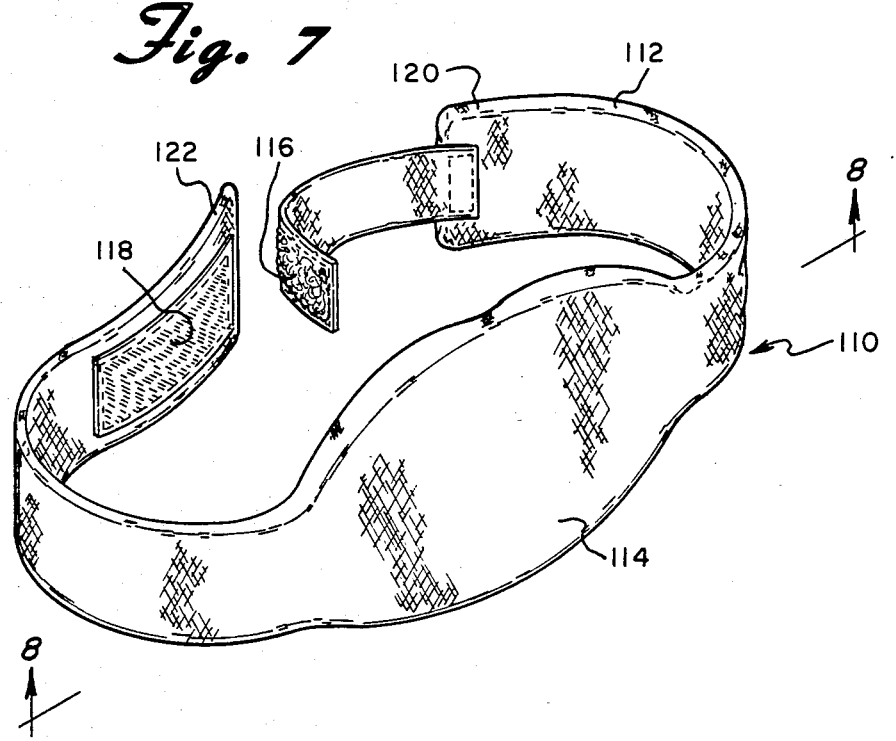
FIG. 7 is a view similar to FIG. 4 but showing a second embodiment of the invention.
Figure 8:
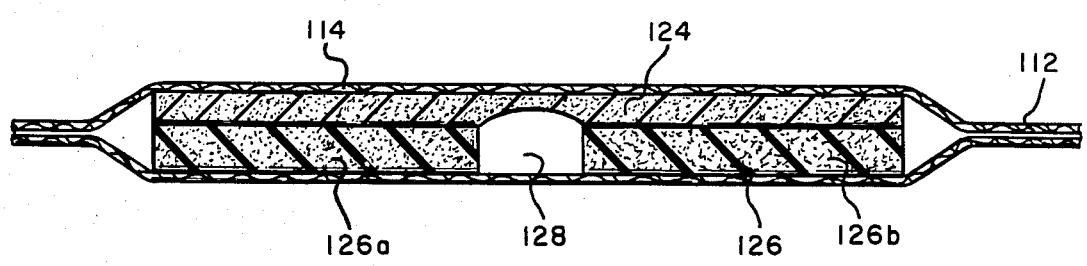
FIG. 8 is a cross-sectional view taken through the line 8—8 of FIG. 7.

A second embodiment of the invention is shown in FIGS. 7 and 8 and is designated generally as 110. Support 110 also includes a belt 112 and a support pad 114 carried by the belt adjacent its mid-portion.

The primary difference between the support 110 and the support 10 is that the pad 114 of support 110 is an integral part of the belt 112. That is, the fabric which forms the belt 112 is a continuous piece of fabric which also covers the foam pad layers 124 and 126. Preferably the fabric which combrises the belt 112 and the cover for the pad 114 is constructed of a lightweight flexible elastic fabric material such as that sold under the trademark Neoprene.

The pads 124 and 126 may be constructed in substantially the same manner as the foam pads 24 and 26. Alternatively, it is also possible to form the groove 128 by utilizing two separate pads 126a and 126b which are spaced apart by approximately 1½ inches. It should be readily apparent that the foam pad 26 of the support 10 can be constructed in a similar manner.

As shown in FIG. 7, the closure for the support 110 is comprised of a single strip of Velcro fastener 118 sewn onto the inner surface of a first end 122 of the belt 112 and a single Velcro fastener 116 attached at its end to the remote end 120 of the belt 112. The Velcro fastener 116, thus, extends outwardly in the form of a tab. This is, however, by way of example only. It should be readily apparent to those skilled in the art that it would also be possible to secure the Velcro fastener 116 to the outer surface of the belt end 120 in the same manner as shown in FIG. 4 with respect to support 10. Furthermore, in lieu of the two strips of Velcro fasteners shown in FIG. 4, a single wider strip such as shown at 118 and 116 could be utilized.

The present invention may be embodied in other specific forms without departing from the spirit or essential attributes thereof and accordingly, reference should be made to the appended claims rather than to the foregoing specification as indicating the scope of the invention.

We claim:

1. A lumbosacral support comprising:

a belt adapted to be worn around a person's waist and including means adjacent the ends thereof for connecting said ends together;

a fabric-covered foam pad carried by said belt intermediate the ends thereof so that said pad is positioned only against a person's lower back when said belt is being worn;

said pad having a vertically extending trough-like groove cut away from the central portion thereof, said groove extending throughout the height of said pad but only partially through the thickness thereof and being positioned such that when said belt is worn, said groove directly overlies and is in substantial alignment with the person's spine whereby when said person presses against a seat back, said foam pad puts pressure on the supporting lumbosacral musculature on either side of the spine but does not put pressure directly on the spinal column.

2. A support as claimed in claim 1 wherein said belt is elastic.

3. A support as claimed in claim 2 wherein each of said layers has a vertically extending trough-like groove therein and in alignment with each other.

4. A support as claimed in claim 3 wherein one of said layers of foam is closer to said person's back when said belt is worn and wherein said other layer is more rigid than said closer layer.

5. A support as claimed in claim 4 wherein said foam layers are bonded together.

6. A support as claimed in claim 1 wherein said connecting means are comprised of Velcro.

7. A support as claimed in claim 1 wherein said pad is comprised of two layers of foam material.

8. A support as claimed in claim 1 wherein said pad has a first surface adapted to be adjacent a person's back and a second surface remote therefrom and wherein said groove is formed in said first surface.

9. A lumbosacral support comprising a belt and a fabric foam pad carried by said belt, said pad being thicker on either side of a vertical central line thereof than at said central line whereby when said belt is worn around a person's waist with said pad positioned only against the lower back and said central line in alignment with the spinal column, said pad puts pressure on the supporting lumbosacral musculature on either side of the spine but does not put pressure directly on the spinal column.

* * * * *